United States Patent
Kabugo et al.

(10) Patent No.: US 10,662,499 B2
(45) Date of Patent: May 26, 2020

(54) TREATMENT OF DEGRADED OXIME METAL EXTRACTANTS IN PROCESS ORGANIC SOLUTIONS

(71) Applicant: OUTOTEC (FINLAND) OY, Espoo (FI)

(72) Inventors: James Kabugo, Pori (FI); Erkki Paatero, Helsinki (FI)

(73) Assignee: OUTOTEC (FINLAND) OY, Espoo (FI)

( * ) Notice: Subject to any disclaimer, the term of this patent is extended or adjusted under 35 U.S.C. 154(b) by 124 days.

(21) Appl. No.: 15/558,792

(22) PCT Filed: Mar. 18, 2016

(86) PCT No.: PCT/FI2016/050169
§ 371 (c)(1),
(2) Date: Sep. 15, 2017

(87) PCT Pub. No.: WO2016/151190
PCT Pub. Date: Sep. 29, 2016

(65) Prior Publication Data
US 2018/0073099 A1    Mar. 15, 2018

(30) Foreign Application Priority Data
Mar. 20, 2015   (FI) ..................................... 20155195

(51) Int. Cl.
*C22B 3/24* (2006.01)
*C22B 3/00* (2006.01)
(Continued)

(52) U.S. Cl.
CPC ................ *C22B 3/24* (2013.01); *B01D 15/02* (2013.01); *B01F 13/1011* (2013.01);
(Continued)

(58) Field of Classification Search
None
See application file for complete search history.

(56) References Cited

U.S. PATENT DOCUMENTS 4,104,359 A * 8/1978 Davis .................... C22B 3/0017
                                                                 423/139
4,507,248 A    3/1985 Mathew et al.
(Continued)

FOREIGN PATENT DOCUMENTS

AU    1989/044515 B    5/1990
CL    200200038       11/2002
(Continued)

OTHER PUBLICATIONS

Machine translation of JP54112377A, pp. 1-2. (Year: 1979).*
(Continued)

*Primary Examiner* — Clare M Perrin
(74) *Attorney, Agent, or Firm* — Buchanan, Ingersoll & Rooney PC

(57) ABSTRACT

The invention relates to a method for regenerating the extractive potential of an organic hydroxyoxime-based extraction solution used in the recovery of metals by liquid-liquid extraction. The method is two-stage, in which a solid hydroxylamine is used in the reaction stage, and the removal of the undesirable compounds generated in the reaction occurs in the second stage by adsorption purification. The method of the invention is suitable for treatment of degraded oxime metal extractants in various process organic solutions both in aldehyde and ketoxime extractant solutions. The method can also be used to treat a mixture of degraded oxime extractants.

21 Claims, 2 Drawing Sheets

(51) Int. Cl.
| | |
|---|---|
| *C22B 3/26* | (2006.01) |
| *C22B 3/12* | (2006.01) |
| *B01J 20/20* | (2006.01) |
| *B01J 20/16* | (2006.01) |
| *B01J 20/14* | (2006.01) |
| *B01J 20/06* | (2006.01) |
| *B01F 17/00* | (2006.01) |
| *B01F 13/10* | (2006.01) |
| *B01F 15/02* | (2006.01) |
| *C22B 3/30* | (2006.01) |
| *B01D 15/02* | (2006.01) |
| *C07C 249/08* | (2006.01) |
| *C07C 249/14* | (2006.01) |

(52) U.S. Cl.
CPC .......... *B01F 17/0042* (2013.01); *B01J 20/06* (2013.01); *B01J 20/14* (2013.01); *B01J 20/16* (2013.01); *B01J 20/20* (2013.01); *C22B 3/0005* (2013.01); *C22B 3/0017* (2013.01); *C22B 3/0021* (2013.01); *C22B 3/12* (2013.01); *C22B 23/04* (2013.01); *B01D 2215/029* (2013.01); *B01F 2215/0036* (2013.01); *B01J 2219/00029* (2013.01); *B01J 2219/00033* (2013.01); *C07C 249/08* (2013.01); *C07C 249/14* (2013.01); *Y02P 10/234* (2015.11)

(56) References Cited

U.S. PATENT DOCUMENTS

| | | | | |
|---|---|---|---|---|
| 5,300,689 A | * | 4/1994 | Krbechek | C07C 251/48 564/259 |
| 5,993,757 A | | 11/1999 | Virnig et al. | |
| 6,432,167 B1 | | 8/2002 | Virnig et al. | |
| 2012/0080382 A1 | * | 4/2012 | Paatero | B01F 7/00441 210/662 |
| 2015/0144540 A1 | | 5/2015 | Paatero et al. | |

FOREIGN PATENT DOCUMENTS

| | | | |
|---|---|---|---|
| CL | 200702326 | | 7/2008 |
| CL | 201000368 | | 9/2010 |
| CL | 201100818 | | 2/2012 |
| CL | 201103102 | | 7/2012 |
| JP | 54112377 A | * | 9/1979 |
| JP | S54-112303 A | | 9/1979 |
| WO | WO 1998/039492 A1 | | 9/1998 |
| WO | 01/14604 A1 | | 3/2001 |
| WO | 2008/021129 A2 | | 2/2008 |
| WO | 2010/044972 A1 | | 4/2010 |
| WO | WO 2010/142841 A1 | | 12/2010 |

OTHER PUBLICATIONS

International Search Report (PCT/ISA/210) dated May 30, 2016, by the European Patent Office as the International Searching Authority for International Application No. PCT/FI2016/050169.
Written Opinion (PCT/ISA/237) dated May 30, 2016, by the European Patent Office as the International Searching Authority for International Application No. PCT/FI2016/050169.
International Preliminary Report on Patentability (PCT/IPEA/409) completed on Feb. 21, 2017, by the European Patent Office as the International Preliminary Examining Authority for International Application No. PCT/FI2016/050169.
Search Report issued by the Chilean Patent Office in corresponding Chilean Patent Application No. 201702319 dated Feb. 11, 2019 (8 pages).

* cited by examiner

TREATMENT OF DEGRADED OXIME METAL EXTRACTANTS IN PROCESS ORGANIC SOLUTIONS

FIELD OF THE INVENTION

The invention relates to a method for regenerating the extractive potential of an organic hydroxyoxime-based extraction solution used in the recovery of metals by liquid-liquid extraction. The method is two-stage, in which a solid hydroxylamine is used in the reaction stage, and the removal of the undesirable compounds generated in the reaction occurs in the second stage by adsorption purification.

BACKGROUND OF THE INVENTION

Liquid-liquid extraction is used generally in metal separation processes, allowing metals to be extracted from aqueous solution using organic extraction solutions. An extraction solution consists of an extraction reagent and a hydrocarbon solvent. The extraction reagent is generally diluted in a hydrocarbon solvent, which dissolves into an aqueous solution or evaporates into air as little as possible in process conditions.

The composition of both the active extraction reagent and its hydrocarbon solvent in the extraction solution has been found to change during long-term industrial use. As a result, the metal-binding power of some extraction reagents may have worsened. In particular this has been observed in copper extraction processes and nickel extraction processes which utilize various reagents based on hydroxyoxime derivatives. These reagents are also used for the extraction of certain other metals and metalloids (e.g. palladium and germanium) as well as in some synergistic extraction reagent mixtures to modify the selectivity for different metals.

It is known that a hydroxyoxime reagent used in extraction degrades in the hydrolysis reaction into aldehyde or ketone and may be reoximated using hydroxylamine ($NH_2OH$) or a salt thereof. The reoximation reaction takes place as follows:

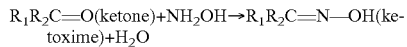

$R_1R_2C=O$(ketone)+$NH_2OH \rightarrow R_1R_2C=N-OH$(ketoxime)+$H_2O$

If $R_2=H$ in the formula, the source material in question is some aldehyde and the product the corresponding aldoxime. If $R_2$ is for example an alkyl or aryl group, it concerns a ketone and ketoxime. This same equilibrium reaction from right to left, in other words acid-catalysed hydrolysis, is one of the decomposition reactions that occur when hydroxyoxime is used as the extraction reagent in the extraction process. However, it is known that hydroxyoximes also decompose e.g. in oxidation reactions.

The effectiveness of the hydroxyoxime reagent present in the organic phase is a crucial factor in the liquid-liquid extraction. Replacement of the organic phase extraction reagents would require significant costs as well as reduced efficiency in the process due to shut down of the process during replacement.

US2012/0080382 describes a method and apparatus for restoring the extractive potential of organic hydroxyoxime-based extraction solution used in the recovery of metals by liquid-liquid extraction. The method is two-stage, in which an aqueous solution of hydroxylamine or some hydroxylamine compound is used in the reaction stage, and the removal of the undesirable compounds generated in the reaction occurs in the second stage by adsorption purification. The reaction stage and the adsorptive stage are carried out in a mixing tank. This liquid-liquid method has been effective for the regeneration of degraded aldoxime type extractants but for ketoxime type reagent it is slow and the conversion remains low after treatment.

Several processes of extraction of metals from aqueous solutions containing metal values in which the degraded circuit organic phase (extractant phase) is reoximated to again restore the effectiveness of the oxime extractant present in the organic phase have been disclosed in the prior art. U.S. Pat. No. 4,104,359 discloses use of solid-liquid reaction mixture in a process for regenerating an active component of an organic extractant. It teaches that organic sulphonic acid causes the degradation of a α-hydroxyoxime reagent in the organic phase and that α-hydroxyoxime can be reoximated in a solid-liquid reaction mixture directly using a solid hydroxylamine salt. The method can also be used for β-hydroxyoximes, which are ketoximes. Said patent mentions that alternatively a saturated aqueous solution of hydroxylamine may be used and the process may be performed for instance in a mixer-settler-type of extraction cell. The method emphasizes percolation of degraded extractant solution past only excess amounts of solid hydroxylamine acid salt as a technique to accomplish the regeneration reaction. The method uses only excess amounts of hydroxylamine salt in absence of an alkali.

U.S. Pat. No. 5,993,757 relates to an improvement in the process of extraction of a metal, the improvement comprising the reoximation of decomposed hydroxyoxime extractant using hydroxylamine salt. In this method distillation will most typically be employed on the organic phase that is recovered from raffinate by coalescers or by skimming it off from ponds. Furthermore, the reaction of the ketone and aldehyde degradant with hydroxylamine will be carried out in the presence of a catalytic amount of a phase transfer catalyst.

U.S. Pat. No. 5,300,689 discloses a process for oximation of carbonyl compounds, such as ketones and aldehydes by oximation with hydroxylamine including oximation processes carried out in the presence of a catalytic amount of an acid phase transfer catalyst, such as 2-ethylhexanoic acid, and/or the presence of an alkali metal or alkaline earth metal catalyst.

Regeneration of degraded oxime extractant in process organic solution has also been disclosed in AU1989044515. However, this method employs a liquid-liquid reaction in presence of aqueous ammonium hydroxide.

The regeneration behaviour of process organic solutions tend to vary from industrial solvent extraction (SX) process to another due to the differences in chemical and physical properties of process solutions and operational practices, among others. In some cases the regeneration reaction can be done in a shorter period of time whereas in others it may require relatively longer residence times. There is a need for an economical and effective process for restoring the extractive potential of organic hydroxyoxime-based extraction solution used in the recovery of metals by liquid-liquid extraction.

BRIEF DESCRIPTION OF THE INVENTION

An object of the present invention is to provide a method so as to alleviate the disadvantages of the prior art. The objects of the invention are achieved by a method which is characterized by what is stated in the independent claims. The preferred embodiments of the invention are disclosed in the dependent claims.

The present invention describes a solid-liquid reaction method for regeneration of degraded ketoxime and aldoxime extractants in process organic solutions. The invention relates to the method disclosed in US2012/0080382, which is incorporated here by reference. The invention is based on the idea of using a solid hydroxylamine sulfate (HAS) instead of an aqueous solution in a two-stage method, in which a solid hydroxylamine or its salt is used in the reaction stage (step a), and the removal of the undesirable compounds generated in the reaction occurs in the second stage by adsorption purification (step b). The adsorption purification is essential for the overall treatment of degraded process organic solutions.

The method takes advantage of the presence of suspended fine solid particles of the reaction mixture thus facilitating faster reaction rates especially in cases of low degree of extractant degradation or low amounts of extractant degradations. It restores the metal loading capacity of the organic phase. The method employs hydroxylamine or salt thereof to proportions nearly equivalent to the stoichiometric amounts of carbonyl compounds (aldehyde and ketones) in the organic phase. The method of the invention also utilizes of much less alkali salt than the prior art methods. The ratio of hydroxyl ammonium sulphate/alkali salt used in the present invention helps to minimize the decomposition of the reacting hydroxylamine (free base) especially in alkaline media.

The method of the invention is suitable for treatment of degraded oxime metal extractants in various process organic solutions both in aldehyde and ketoxime extractant solutions. The method can also be used to treat a mixture of degraded oxime extractants. The present application shows that method of the invention is far more effective than the prior art liquid-liquid method for treatment of degraded oxime metal extractants.

The method reduces chemical reagent consumption in extractant regeneration. Considering relatively low solid content requirement in the regeneration reactors, the organic treatment capacity of the present method is high. The method also minimizes water consumption since it operates with a solid-organic mixture. The method does not require extensive instrumentation and thus it can be easily operated.

BRIEF DESCRIPTION OF THE DRAWINGS

In the following the invention will be described in greater detail by means of preferred embodiments with reference to the attached [accompanying] drawings, in which.

DETAILED DESCRIPTION OF THE INVENTION

Figure 1:
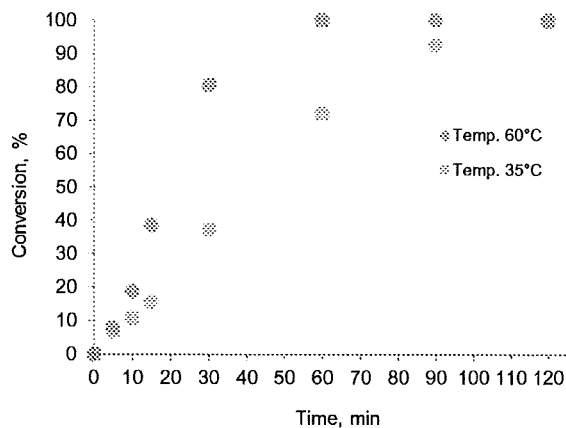
FIG. 1 is a graphical presentation of the progress of the regeneration reaction at temperatures of 35° C. and 60° C. The process organic solution with about 1.5 wt % aldehyde degradate was treated.

The invention relates to a method for treating an organic extraction solution used in liquid-liquid extraction, wherein the metal extraction properties of the organic extraction solution have changed chemically under process conditions.

The organic extraction solution comprises of an extraction reagent and a hydrocarbon solvent, whereby the active metal-binding component of the extraction reagent is a hydroxyoxime derivative, whose oxime group is either an aldoxime or ketoxime in structure. In addition to these the organic extraction solution may comprise an organic modifying agent that belongs to at least one of the groups: alcohol, phenol, ester, diester, ether, diether, ketone, amide or nitrile.

In order to regenerate the physical and metal extraction properties of the extraction solution essentially to the original level, the two stage regeneration treatment of the extraction solution comprises the steps of (a) contacting the organic extraction solution with a wetted hydroxylamine or salt thereof in its solid form in the presence of little amounts of solid alkaline salt and thereafter removing the solid particles from the organic extraction solution, and (b) purifying the organic extraction solution by adsorption purification by bringing said organic extraction solution into contact with an adsorption material in a solid form. In the first step the aldehydes and/or ketones formed in the extraction solution in process conditions are reoximated. The second step enables the purification of the extraction solution from the compounds of harmful substances generated in the reaction stage and thus facilitates faster settling or separation of the aqueous and organic phases.

The reoximation reagent is solid hydroxylamine, most preferably hydroxylamine sulphate i.e. hydroxyl ammonium sulphate $(H_2NOH)_2H_2SO_4$. It is generally available commercially in a solid form. The amount of hydroxylamine or its acid salt used in the reaction stage is nearly equivalent to the stoichiometric amounts of aldehyde and/or ketone formed in the extraction solution. In the present method no phase transfer catalyst is used to accelerate the reaction nor is there distillation before hydroxylamine treatment as disclosed in U.S. Pat. No. 5,993,757, but instead the removal of impurities takes place after the reaction stage by adsorption purification.

The reoximation reagent is used in the presence of little amounts of alkali salt, such as an alkali metal hydroxide, an earth alkali metal hydroxide, an alkali metal carbonate, an earth alkali metal carbonate or ammonia. Most preferably solid alkaline salt is sodium carbonate (soda ash). The addition of small amounts of alkali salt provides enough free base for the reoximation reaction at the same time minimizing decomposition of hydroxylamine especially at high reaction temperatures. A stoichiometric amount of alkali salt, or an amount of slightly below the stoichiometric amount, is preferable in order to maintain the pH of the organic extraction solution just below the neutral value. The mass ratio of HAS/soda ash is preferably in the range of 1.4:1-3:1. Technically a mass ratio of 1.5:1 is even more preferable for many process organic cases. This is enough to neutralize most of the acid in the hydroxylamine salt. Basically there is no need for excess carbonate. A higher HAS/Soda ash ratio value which is at least within the range of 3:1 can be applied especially where higher oximation reaction temperatures are required (e.g. 60-90° C.) for a ketone. This helps to minimize the decomposition of the reacting hydroxylamine (free base) especially in alkaline media.

The temperature of the reaction may vary preferably from 35-70° C. depending on the condition of the process organic and whether the extractant degradate is an aldehyde or a ketone. An aldehyde is preferably oximated at temperatures of 35-45° C., for a ketone a temperature of 60-70° C. is more preferable. Typically the required residence time in the regeneration reactors is less than an hour. The reaction time may be under 6 minutes at the shortest, but typically it is between 10-90 min. For most process organic solutions the residence time is maximum 2-4 h.

The regeneration process can be operated as a batch in stirred batch reactors or in a continuous flow operation using continuous stirred reactors. The reaction stage and the adsorption stage may take place as either a batch operation or a continuous operation or a combination of them. In the regeneration reactors, barren organic from a solvent extraction (SX) process containing degraded oxime extractant is reacted with wetted hydroxyl ammonium sulfate (HAS) in its solid form in presence of little amounts of solid alkaline salt. The solid-organic mixture is vigorously stirred and solid particles are dispersed into the organic phase. Limited amount of water is then added for wetting HAS/sodium carbonate solids to aid neutralization of HAS with alkali salt. Mass ratio of HAS/water is 3 to 10. A preferable mass ratio is 5 to 7.

The present method, like the related prior art method disclosed in US2012/0080382 A1, is a two-phase liquid-liquid reaction so the reaction requires continuous effective mixing of the dispersion formed of the solutions. In the present invention the suspended fine solid particles of the reaction mixture facilitate faster reaction rates when compared to the prior art method. Water is added to the reaction mixture only for minimal wetting of solid particles.

After the reoximation reaction, the organic extraction solution is sent to a decanter or filter to remove any solid particles. The solids removed are mainly sodium sulfate and can be directly discharged to the SX process waste treatment area. However, alternatively, after the reoximation reaction, the organic extraction solution maybe first washed with an aqueous solution at a desirable pH of 2-5 and temperature of about 25-40° C. The washing can be carried out using a one stage mixer-settler unit or with only a mixer and the phases separated with use of a centrifuge or decanter. The washing stage is beneficial for a continuous process for recycling of any hydroxylamine and it may also serve as an exit route for the sodium sulfate salt from the regeneration reactors.

The reoximated organic extraction solution is then sent to an adsorption purification stage as described in US2012/0080382 A1. In this stage the extraction solution is purified of the side-products generated in the hydroxylamine reaction by means of a solid, and ground adsorbent material. Preferably the adsorbent material is fine-ground. Adsorption material may also be fed into the adsorption stage in powder, spherical or fibre form. The adsorption material in a solid form is preferably at least one of the following: bentonite, diatomite, aluminium silicate, metal oxide, activated carbon, polymeric adsorbent or polymeric ion exchange resin. The purpose of the adsorbent is to remove the undesired compounds from the solution phase onto the surface of the adsorption material.

Adsorption purification may be implemented either in the same reactor as the reaction stage or in another separate reactor vessel after it. The mixing in the adsorption stage should also be effective, because for instance bentonite forms a viscous suspension to some extent with the extraction phase. The proportion of adsorbent in the suspension is between 0.01 and 10 weight %, preferably at least between 0.5 and 3 weight %. Afterwards the adsorbent is separated from the organic extraction solution for instance by settling, filtration or centrifugation and the treated extraction solution can be returned to the metal recovery process. It should be noted that adsorption purification is critical in the overall treatment of degraded process organic solution in order to remove the surface-active impurities that affect the settling of the phases. The aqueous and organic phases settle or separate from each other far faster than solutions that have not been subjected to adsorption purification.

EXAMPLES

Example 1

This case illustrates by laboratory experiments the performance of the regeneration method in treating organic solutions with low amounts of degraded extractant and analyzes the effect of temperature. The example also highlights the performance of the adsorption purification stage. For the reoximation test, a portion of process organic solution which contained an estimated aldehyde degradate, 5-nonylsalicylaldehyde, equivalent to 1.5 wt. % of the total organic weight and corresponding to an extractant degradation degree of 14% was first stripped with 180 g/L $H_2SO_4$ to remove metal impurities. Then 472 mL of stripped organic was measured into a one liter batch laboratory glass reactor and the organic temperature was raised to 35° C. 16.5 g of HAS was added followed by 3 g of distilled water. The mixture was then gently stirred while 5.3 g of soda ash was introduced into the reactor. After addition of $Na_2CO_3$, the contents were vigorously stirred (about 750 rpm) and the experiment was left to run for 2 h while taking samples at different time intervals. The samples were filtered and analyzed for aldehyde/oxime ratio on a gas chromatograph. The bulk of the reoximated organic was recovered in a glass flask and immediately washed with an acidified aqueous solution (pH 2) at 40° C., with an organic/aqueous phase ratio of 1 for 3 minutes. The phases are then separated using separating funnels and organic filtered through hydrophobic filter papers. Final organic was analyzed on a gas chromatograph for aldehyde/oxime ratio and also tested for copper loading against the original process organic solution. A parallel test was repeated at a reaction temperature of 60° C. under similar conditions. Reoximation results are shown in FIG. 1.

Organic after reoximation was subjected to the adsorption purification step. The purification of reoximated extractant solution was performed as follows: 450 mL of organic solution was put into a one liter laboratory glass reactor at room temperature followed by addition of 4.5 g of dry bentonite adsorbent. The contents were gently mixed for half an hour. After which, the organic was decanted and filtered to remove any suspended solids. Then copper extraction phase disengagement test in organic continuity and copper loading capacity test were examined at room temperature for both bentonite treated organic and original process organic solution. The results are given in Table I.

FIG. 1 presents the progress of the oximation reaction. Despite the fact that the amount of extractant degradate in the organic phase was relatively low, the reoximation reaction progressed steadily to completion. It can be observed that even at a lower temperature (35° C.), the reaction was complete (100%) after 2 h. The reaction rate was faster with increase in temperature. Over 85% reaction conversion was achieved in about 30 minutes at 60° C. and complete conversion within an hour.

It can be observed in Table I that the copper loading capacity of the organic phase increased after the 2 h oximation tests. The disengagement after reoximation are quite slow, but we can see that the impurities formed during reagent were effectively removed by adsorption purification treatment and the disengagement rate is improved. Thus overall results assert the significance of reoximation and adsorption purification stages in regeneration of degraded extractant solution while using this process method.

TABLE I

Copper loading capacity and extraction phase disengagement times

| Sample details | Copper loading, g/L | | Phase disengagement time, s | |
|---|---|---|---|---|
| | Reox. Temp. 35° C. | 60° C. | Reox. Temp. 35° C. | 60° C. |
| Process organic | 9.4 | 9.3 | 69 | 95 |
| Reoximated organic | 10.7 | 12.3 | >200 | >200 |
| Bentonite treated reoximated organic | 11.1 | 11.6 | 40 | 53 |

Example 2

The second example continues to emphasize the effectiveness of the treatment method in recovery of degraded extractant, 5-nonylsalicylaldoxime, from relatively dilute process organic extractant solutions. The tested industrial organic contained about 2.0 wt. % aldehyde degradate accounting for an extractant degradation degree of 17%. The organic was first thoroughly stripped with 180 g/L $H_2SO_4$ to remove metal impurities. The reoximation reaction was performed as described in Example 1. Also two parallel tests were again conducted at 35° C. and 60° C.

Figure 2:
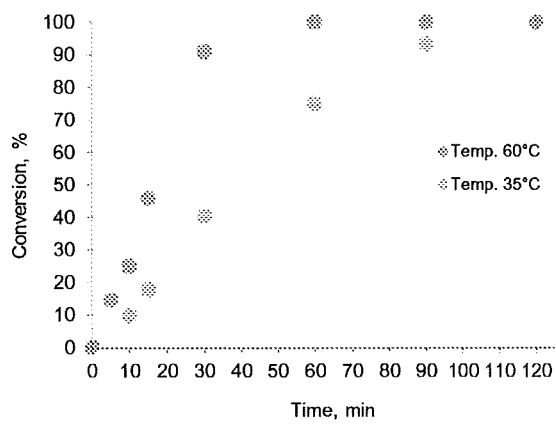
FIG. 2 is a graphical presentation of the progress of the regeneration reaction at temperatures of 35° C. and 60° C. The process organic solution with about 2.0 wt % aldehyde degradate was treated.

FIG. 2 shows the performance of reoximation method at 35° C. and 60° C. Here we see that the reaction rate was relatively comparable to that given in Example 1. We can see again that reaction proceeded steadily to completion, with the higher temperature providing faster reaction rate. The reaction conversion reached over 90% in half an hour at 60° C. and completed within an hour.

Similarly to Example 1, the performance of adsorption purification stage was investigated using the same experimental and analytical methods as described in Example 1. The results are displayed in Table II where it can be observed that copper loading of process organic significantly improved after 2 h reoximation. Also the organic phase separation properties under copper solvent extraction conditions were maintained after adsorption treatment.

TABLE II

Copper loading capacity and extraction phase disengagement times

| Sample details | Copper loading, g/L | | Phase disengagement time, s | |
|---|---|---|---|---|
| | Reox. Temp. 35° C. | 60° C. | Reox. Temp. 35° C. | 60° C. |
| Process organic | 10.6 | 10.4 | 103 | 89 |
| Reoximated organic | 13.0 | 13.2 | >200 | >200 |
| Bentonite treated reoximated organic | 12.8 | 13.1 | 57 | 48 |

Example 3

This example illustrates that the reoximation method can be applied to degraded ketoxime extractant in process organic solution. The tested process organic contained about 4.0 wt. % of 2-hydroxy-5-nonyl acetophenone, representing extractant degradation degree of approximately 20%. The organic was first washed with 180 g/L $H_2SO_4$ before oximation of the extractant degradate. Reoximation of degraded extractant was performed in a 1 liter batch reactor with a total organic volume of 300 mL treated in a single experiment. The organic solution temperature was first adjusted to 60° C. while inside the batch reactor.

Addition of reagents was carried out as follows: 83.7 g of hydroxylamine sulfate (HAS) was added to the organic solution, followed by 15 g of distilled $H_2O$ and finally intermittent addition of 60 g of soda ash while mixing the organic mixture gently. After complete addition of reagents to the organic solution, the contents were vigorously stirred at 750 rpm and the test was left to run for 4 h. Thereafter organic was separated from the reaction mixture by decantation and then washed with acidified water solution of pH 2 at 40° C., with a phase ratio of 1 and a residence time of 3 minutes. The washing was done twice under similar conditions. Washed reoximated organic was filtered and a portion was analyzed on a gas chromatograph to observe the extent of the reoximation reaction. Also copper loading capacity of the organic phase was tested in the same way as described in the above examples.

The extent of the reoximation reaction is given in Table III, alongside the corresponding copper loading capacity of the organic solutions. We can observe that the reaction proceeded quite well, with over 98% conversion attained in 4 h. Furthermore, it can be seen that copper loading capacity of the organic greatly improved, a reflection of the recovered extractant after reoximation. Therefore we can justify that the method can also be used to treat degraded ketoxime extractant in process organic solutions.

TABLE III

Reaction progress and copper loading capacity

| Sample details | Reoximation conversion, % | Copper Loading, g/L |
|---|---|---|
| Process organic | | 13.2 |
| Reoximated organic | 98.4 | 17.7 |

Example 4

The recovery of degraded ketoxime extractant was further demonstrated with use of a synthetic ketoxime extractant solution. Here the purpose was to achieve high reaction conversion in a shorter period of time. In this case, a laboratory degraded authentic commercial ketoxime reagent, 2-hydroxy-5-nonyl acetophenone, was reoximated. The ketoxime degradation degree was equivalent to 28% of the original oxime extractant in the freshly prepared organic solution corresponding to a ketone concentration close to 6.5 wt %.

Reoximation tests were conducted in 1 liter batch reactor with an organic volume of 500 mL treated in each batch. The reaction temperature was maintained at 70° C. The reagents were added into the organic in the following manner: 45 g of HAS, 29 g of sodium carbonate and followed by 10 g of distilled water. The resultant mixture was stirred at 750 rpm for 1.5 h. In this particular example, the washing step after reoximation was skipped. Thus organic was only filtered and analyzed on a gas chromatograph as described in the previous cases. Copper loading capacity was again examined by performing a copper loading test similarly to earlier examples.

According to Table IV, the performance of the reoximation method again was reflected by copper loading capacity. Moreover, this example also showed that the washing stage proposed in this method after reoximation is optional.

TABLE IV

Reaction progress and copper loading capacity

| Sample details | Reoximation Conversion, % | Copper loading, g/L |
|---|---|---|
| Authentic reagent | | 22.3 |
| Degraded authentic reagent | | 16.8 |
| Reoximated organic | 75.1 | 23.8 |

Example 5

This example continues to emphasize the importance of this reoximation method in treatment of degraded ketoxime extractant. The degraded organic solution studied was exactly the same as in Example 4. The tests were done under similar conditions as described in Example 4 except that the reaction temperature was maintained at 60° C. and the batch experiment was run for 2 h. The reoximation reaction was monitored with use of a gas chromatograph and copper loading tests as discussed in previous examples.

In order to demonstrate the significance of the present method, a parallel test was done according to the earlier liquid-liquid reoximation method described in US20120080382. About 472 mL of organic was reoximated in a single batch at 60° C. and mixing rate of 750 rpm. Here samples of dispersion were drawn off at different time intervals, phases separated and organic analyzed in the same way as above.

Table V shows the performance of both reoximation techniques. We can see that the present method was far more effective than the liquid-liquid method. These results further underline the fact that the proposed method can be used to recover degraded ketoxime extractant in process solutions.

TABLE V

Reoximation progress and copper loading capacity for degraded ketoxime reagent

| | Reoximation Conversion, % | | Copper loading, g/L | |
|---|---|---|---|---|
| Sample details | Solid-Liquid | Liquid-liquid | Solid-Liquid | Liquid-liquid |
| Authentic reagent | | | 22.3 | 22.3 |
| Degraded authentic reagent | | | 16.8 | 16.8 |
| Reoximated organic | 57.2 | 3.3 | 20.0 | 17.5 |

Example 6

This example demonstrates that the method can also be used to treat a mixture of degraded oxime extractants such as a combination of degraded 5-nonylsalicylaldoxime and 2-hydroxy-5-nonyl acetophenone. This blend of extractant is commonly available as an authentic mixed reagent. For this given example, the selected original commercial reagent contained both extractants in a ratio relatively close to unit. Similarly to the preceding case, a fresh organic solution was prepared and thereafter degraded in the laboratory. The estimated total composition of extractant degradates was about 10 wt. % which represented a degradation degree of nearly 50% of the original reagent (both aldoxime and ketoxime) in the organic phase. The aldehyde contributed the highest proportion of extractant degradate (equivalent to over 85% of the original aldoxime). In regard to the ketone, the observed ketoxime degradation degree was approximately 18%. This implies that degraded organic mainly contained aldehyde degradate but with significant amounts of a ketone product.

Figure 3:
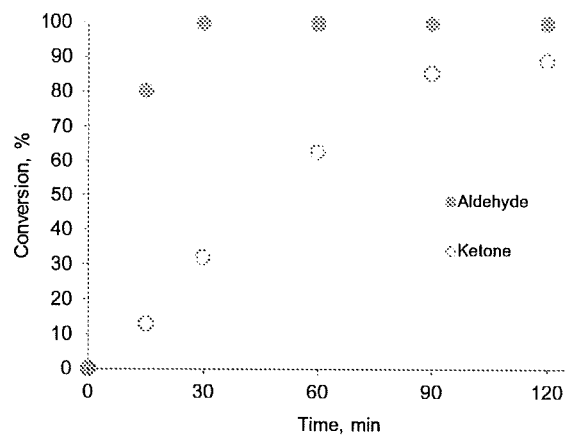
FIG. 3 is a graphical presentation of the extent of the reaction with time at 60° C. An aldehyde/ketone mixture of degraded oxime extractants was treated with the method of the invention.

Batch reoximation was carried out in a 1 liter batch reactor with 500 mL of organic solution treated in each case. The temperature of the organic solution was raised to 60° C. and reagents were added as follows: 70 g of HAS, 46 g of sodium carbonate and lastly 10 g of distilled water. The reactor contents were stirred at 750 rpm for a maximum of 2 h at 60° C. Organic samples were taken at different time intervals, filtered and analyzed on a gas chromatograph. FIG. 3 illustrates the extent of the reaction with time. Complete reoximation of degraded aldoxime was achieved within half an hour. Also very high (>80%) ketoxime recovery was obtained in a residence time of 2 h.

Figure 4:
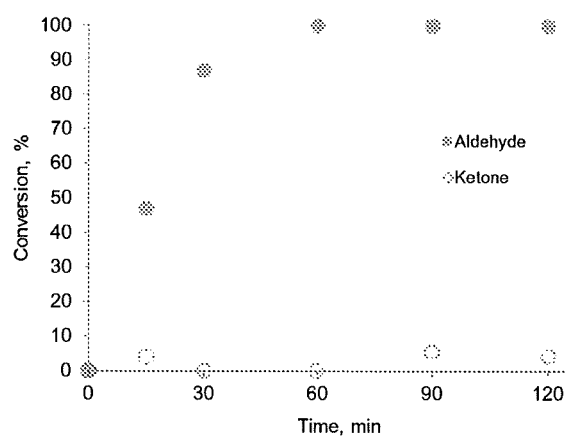
FIG. 4 is a graphical presentation of the progress of the regeneration reaction as in FIG. 3 but performed according to the liquid-liquid method described in US20120080382.

The reoximation test was also performed according to liquid-liquid method described in US20120080382. Here, 472 mL of organic was treated in a single batch for 2 h and at 60° C. and samples of dispersion were drawn off at different time intervals. The samples were filtered through hydrophobic filter papers and analyzed similarly as mentioned above. The results are displayed in FIG. 4, where it can be observed that the ketone responded poorly to the reoximation method. At the same time we again see that, also the reoximation of degraded aldoxime extractant was much slower than in FIG. 3.

From Table VI, we can clearly see that metal loading capacity of the organic solution was restored after reoximation with use of the present solid-liquid method. On the other hand we also see that full copper loading capacity fell short while using the liquid-liquid method which is detailed in US20120080382. Thus we can conclude that, the proposed solid-liquid method can be able to treat such degraded mixed extractant reagents in process solutions.

TABLE VI

Copper loading capacity

| | Copper loading, g/L | |
|---|---|---|
| Sample details | Solid-Liquid | Liquid-liquid |
| Authentic reagent | 20.3 | 20.3 |
| Degraded authentic reagent | 10.1 | 10.1 |
| Reoximated organic | 20.3 | 19.6 |

It will be obvious to a person skilled in the art that, as the technology advances, the inventive concept can be implemented in various ways. The invention and its embodiments are not limited to the examples described above but may vary within the scope of the claims.

The invention claimed is:

1. A method of regenerating ketone and aldehyde oxime degradation products of a degraded hydroxyoxime based organic extraction solution used in the recovery of metals by liquid-liquid extraction, comprising the step of (a) contacting the degraded hydroxyoxime based organic extraction solution comprising the ketone and aldehyde oxime degradation products with a wetted hydroxylamine or salt thereof in solid form in the presence of a solid alkaline salt to obtain a solid-organic mixture and thereafter removing any solid particles from the degraded hydroxyoxime based organic extraction solution, and the step of (b) purifying the organic extraction solution by adsorption purification by bringing said degraded hydroxyoxime based organic extraction solution into contact with an adsorption material in solid form,
wherein the method is performed without the use of a phase transfer catalyst.

2. The method according to claim 1, wherein in step (a) the solid-organic mixture is stirred and solid particles are dispersed into the degraded hydroxyoxime based organic extraction solution.

3. The method according to claim 1, wherein the solid hydroxylamine or salt thereof is at least one selected from the group consisting of: hydroxylamine sulphate, hydroxylamine halide, hydroxylamine phosphate, or hydroxylamine sulphonate.

4. The method according to claim 1, wherein the quantity of hydroxylamine used in step (a) is at least the stoichiometric equivalent of the total quantity of aldehyde and/or ketone formed in the extraction solution as hydroxyoxime degradation products.

5. The method according to claim 1, wherein the solid alkaline salt is selected from the group consisting of: alkali metal hydroxide, earth alkali metal hydroxide, alkali metal carbonate, alkali earth metal carbonate, and ammonia.

6. The method according to claim 1, wherein the solid alkaline salt is sodium carbonate.

7. The method according to claim 1, wherein any solid particles are removed from the organic extraction solution by a decanter or filter.

8. The method according to claim 1, wherein after contacting the organic extraction solution with the wetted hydroxylamine or salt thereof in solid form in the presence of the solid alkaline salt and prior to the removal of the solid particles, the organic extraction solution is washed with an aqueous solution.

9. The method according to claim 8, wherein the washing is done at a pH of 2-5 and temperature of about 25-40° C.

10. The method according to claim 8, wherein the washing is carried out using a one stage mixer-settler unit or with only a mixer and the aqueous solution and the organic extraction solution are separated with a centrifuge or decanter.

11. The method according to claim 8, wherein the hydroxylamine or its salt is recycled after the washing.

12. The method according to claim 1, wherein the adsorption material in a solid form is at least one selected from the group consisting of: bentonite, diatomite, aluminium silicate, metal oxide, activated carbon, polymeric adsorbent, and polymeric ion exchange resin.

13. The method according to claim 1, wherein the quantity of adsorption material is 0.01-10 weight % based on the degraded hydroxyoxime based organic extraction solution.

14. The method according to claim 1, wherein the quantity of adsorption material is 0.5-3 weight % based on the degraded hydroxyoxime based organic extraction solution.

15. The method according to claim 1, wherein the adsorption material is separated from the degraded hydroxyoxime based organic extraction solution by settling, filtration or centrifugation.

16. The method according to claim 1, wherein the adsorption material is in ground form.

17. The method according to claim 1, wherein the adsorption material is a powder, spheres or filaments.

18. The method according to claim 1, wherein the step (a) and the step (b) take place as a batch operation.

19. The method according to claim 1, wherein the step (a) and the step (b) take place as a continuous operation.

20. The method according to claim 1, wherein the step (a) takes place as a batch operation and the step (b) takes place as a continuous operation.

21. The method according to claim 1, wherein the step (a) takes place as a continuous operation and the step (b) takes place as a batch operation.

\* \* \* \* \*